United States Patent [19]

Merrill, deceased et al.

[11] Patent Number: Plant 6,294

[45] Date of Patent: Sep. 20, 1988

[54] APPLE TREE "MERRIGOLD"

[76] Inventors: Grant Merrill, deceased, late of Red Bluff, Calif.; by Lucille B. Merrill, legal representative, 325 Breese Ave., Red Bluff, Calif. 96080

[21] Appl. No.: 926,718

[22] Filed: Nov. 4, 1986

[51] Int. Cl.[4] ..... A01H 5/03

[52] U.S. Cl. ..... Plt./34

[58] Field of Search ..... Plt. 34

*Primary Examiner*—Robert E. Bagwill

*Attorney, Agent, or Firm*—Worrel & Worrel

[57] ABSTRACT

A new and distinct Apple Tree denominated varietally as "Merrigold", generally resembling the Golden Delicious Apple Tree (unpatented); but bearing fruit having a yellow-green skin and yellow-white flesh and which is mature for harvesting approximately mid-August; approximately 1 month earlier than that of the Golden Delicious Apple Tree, at Dordogne, France.

1 Drawing Sheet

BACKGROUND OF THE INVENTION

The present invention relates to a new and distinct variety of apple tree denominated varietally as "Merrigold"; and which is somewhat similar in physical characteristics to the Golden Delicious Apple Tree (unpatented) from which it was derived as a progeny after the successful cross-pollenization of the Golden Delicious Apple Tree with a Yellow Transparent Apple Tree (unpatented); but from which it is distinguished as to novelty by bearing fruit that is mature for harvesting approximately one month earlier than the Golden Delicious variety at Dordogne, France.

The Golden Delicious Apple Tree (unpatented) is well known as a vigorous producer having firm fruit. Furthermore, the fruit of the Golden Delicious Apple Tree has long been known for its excellent eating quality and delicious flavor.

It has long been recognized that it would be desirable to have an Apple Tree that somewhat resembles the Golden Delicious Apple Tree and its fruit, but which bears fruit which ripens for harvesting earlier in the season, whereby the commercial demand for fruit of such an apple tree can be effectively satisfied over a greater period of time.

ORIGIN AND ASEXUAL REPRODUCTION OF THE NEW VARIETY

The new and distinct variety of Apple Tree hereof was the progeny of a successful cross-pollination between the Golden Delicious variety of apple tree (unpatented) and the Yellow Transparent variety of apple tree (unpatented); the cross being performed by the inventor Grant Merrill, now deceased, on the inventor's property located at Grant Merrill Orchards, on Gilmore Ranch Road, Red Bluff, Calif. The new and distinct variety of apple tree which was produced as a result of this cross-pollination was observed at that time to have the desirable characteristics described. The inventor, thereafter, successfully asexually reproduced the distinct variety by budding it into test trees on his property located at Red Bluff, Calif. The first successful asexual reproduction took place in 1968.

Bud wood procured from the first successful asexual reproduction was thereafter procured by the inventor and was transmitted, in September, 1968 to the Institut National De La Recherche Agronomique, Station de Recherche d'Arboriculture Fruitiere, Domaine du Bois l'Abbe, Beaucouze, 4900 Angers, France for further testing, and for the development of a virus free strain for commercialization. This bud wood was budded into test trees by employees of the Institute for purposes of asexual reproduction and further experimentation. These latter asexual propagations resulted in progeny being produced which were found to possess the same distinctive characteristics as the original offspring.

SUMMARY OF THE NEW VARIETY

The Merrigold Apple Tree is characterized by many of the desirable features of the Golden Delicious Apple Tree (unpatented), but has the important distinction of bearing fruit that is ripe for harvesting approximately one month earlier than the Golden Delicious; and which furthermore has fruit having the same colored flesh as the Golden Delicious variety, but whose skin is more waxen, and has slightly more lenticels that the Golden Delicious.

BRIEF DESCRIPTION OF THE DRAWING

The accompanying drawing is a color photograph of four mature fruit of the subject variety, one of which has been divided in the axial plane, and another being divided transverse to the axial place to show the flesh and seed characteristics; together with a twig bearing representative leaves which display the ventral and dorsal coloration thereof, and two apples showing their external colorations sufficiently matured for harvesting and shipment.

DETAILED DESCRIPTION

Referring more particularly to the pomological details of this new and distinct variety of Apple Tree; the following has been observed under the ecological conditions prevailing at the applicant's agent's orchard, S.S.C.A. Domaine de Castang; located at St. Laurent des Vignes, 24100 Bergerac (Dordogne), France. All major color code plate identifications are by reference to the Inter-Society Color Council, National Bureau of Standards. However, common color names are also employed occasionally.

TREE

Size:

*Generally.*—Medium.

Figure: The variety displays the growth characteristic of being slightly more spreading than the Golden Delicious Variety of Apple Tree (unpatented).
Vigor: Average; and Hardy.
Productivity: Very productive; normal growth.
Regularity of bearing: Regular.
Trunk:
*Size.*—Average.
*Surface texture.*—Variable; Medium to Smooth.
Branches:
*Thickness.*—Average.
*Surface Texture.*—Smooth.
*Color.*—Gray.
Lenticels:
*Number.*—Average; However, the variety displays greater numbers of lenticels as compared with the Golden Delicious variety of Apple Tree.
*Size.*—Medium.
Leaves:
*Size.*—Generally — average.
*Length.*—Approximately 8.5 cm.
*Width.*—Approximately 5.25 cm.
*Color.*—Dorsal color; yellowish green [137.d.y.G].
*Color.*—Ventral color; yellow green [120 M.Y.G.].
*Form.*—Taper-pointed.
*Thickness.*—Average.
*Surface texture.*—Slightly rugose.
*Marginal form.*—Glandular and finely serrate.
*Petiole — length.*—Approximately 2.61 cm.; average as compared with other varieties.
*Petiole color.*—Yellow green [120 M.Y.G.].
*Thickness.*—Variable; slender to average.
Flowers:
*Date of Bloom.*—Approximately the same date of bloom as that of the Golden Delicious Variety Apple Tree (unpatented); at Dordogne, France.
*Size.*—Large, as compared with other Apple varieties.
*Color.*—Dorsal surface — white; However some slight pink coloration may be found in a portion of the petal. The blossom color is not particularly distinctive as compared with other varieties of Apple Trees.
*Fertility.*—Fertile.

FRUIT

Maturity:
*Ripe for Harvesting.*—Approximately mid-August, in Sud-Ouest, Dordogne, France.
*Length of Season.*—Short; the variety hangs well on the tree.
Size:
*Generally.*—Average.
*Axial diameter.*—Approximately 76.35 cm.
*Diameter transverse to the axial plane.*—Approximately 75.25 cm.
*Shape.*—Conical and occasionally rounded.
*Uniformity.*—Uniform.
*Symmetry.*—Symmetrical.
Stem:
*Size.*—Average; approximately 1.5 to 2 cm. in length.
*Thickness.*—Medium.
*Color.*—Greenish Yellow Olive — [106.1.01].
Cavity:
*Depth.*—Average.
*Width.*—Medium to broad.
*Surface texture.*—Smooth.
*Symmetry.*—Symmetrical.
Calyx: Closed.
Lobes:
*Length.*—Short to medium.
*Width.*—Average.
*Form.*—Acute.
Basin:
*Depth.*—Variable — medium to Deep.
*Width.*—Narrow to average.
*Symmetry.*—Symmetrical.
*Surface texture.*—Smooth; however occasionally a russetted texture is evident.
Skin:
*Thickness.*—Variable; Thin to Average.
*Texture.*—Smooth and Waxen.
*Color.*—Yellow Green [116. brill Y G].
*Dots.*—Numbers — average; Size — medium; Color — russett; the color is not distinctive, however.
*Position.*—Areolar.
Flesh:
*Color.*—Yellowish — white [89.p Y].
*Firmness.*—Firm.
*Juice production.*—Juicy; sweet; and subacid.
*Quality.*—Good to very good.
Core:
*Size.*—Small to medium.
*Form.*—Open; and axile.
Core-lines: Meeting.
Calyx-tube:
*Length.*—Variable; narrow to medium.
*Width.*—Narrow to average.
*Form.*—Conical.
Seeds:
*Size.*—Medium to large.
*Form.*—Tufted, and plump.
Use: Fresh market.
Keeping quality: Good.
Resistance to insects: Average.
Resistance to diseases: Average as compared to other varieties.
Shipping quality: Good.

Although the new variety of Apple Tree possesses the desirable characteristics noted under the growing conditions prevailing in Dordogne, France, it is to be understood that variations of the usual magnitude and characteristics incident to changes in growing conditions; fertilization; pruning; and pest control are to be expected.

Having thus described and illustrated my new variety of Apple Tree, what I claim as new and desire to secure by Plant Letters Patent is:

1. A new and distinct variety of Apple Tree substantially as illustrated and described which is characterized by bearing a fruit having a yellow-green skin and yellow-white flesh and by its general resemblance to the Golden Delicious variety Apple Tree (unpatented), but from which it is distinguished therefrom by bearing fruit which matures for harvesting approximately mid-August at Dordogne, France, approximately 30 days earlier than the Golden Delicious variety Apple Tree and by having a tree form which is slightly more spreading than the Golden Delicious Apple Tree.

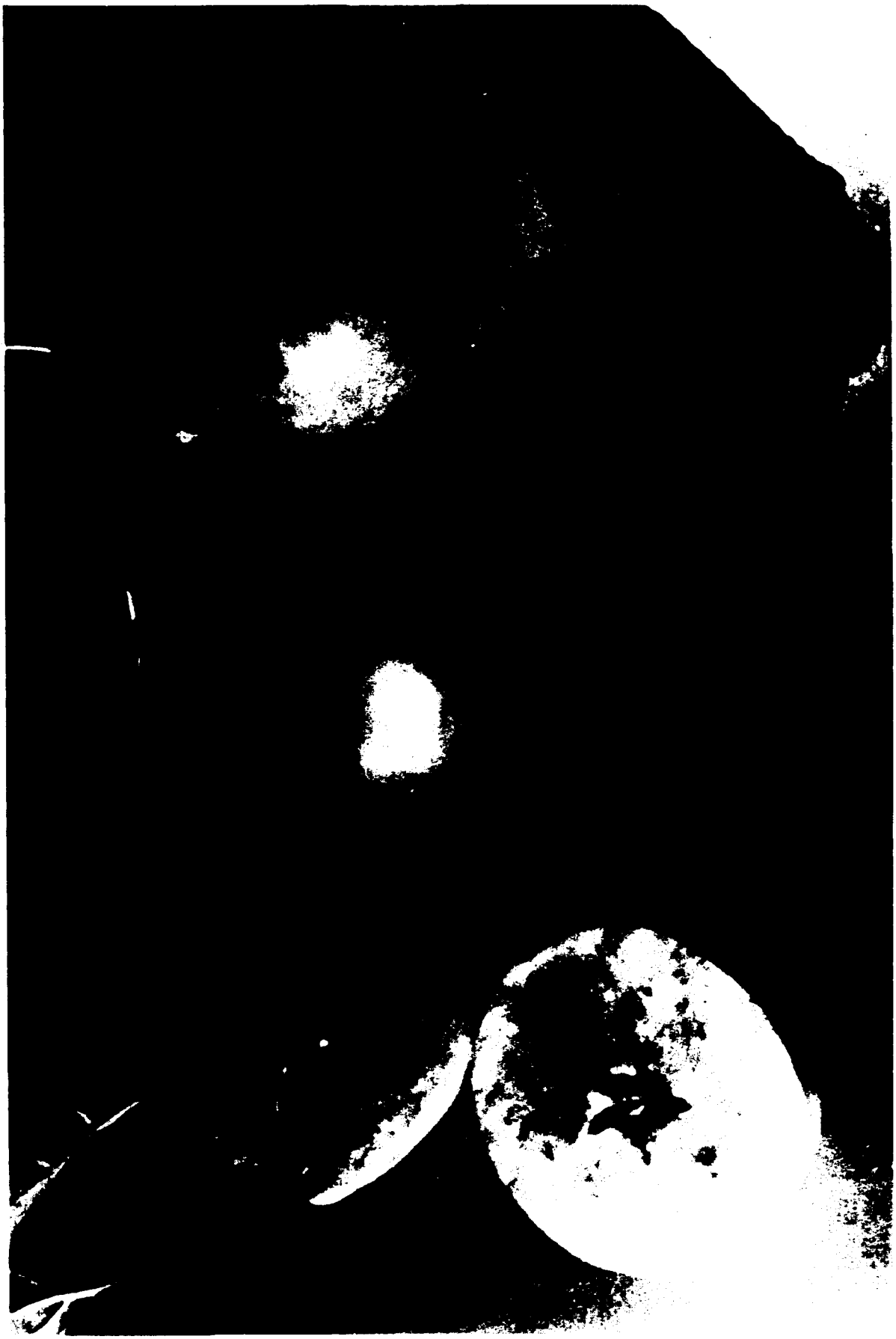

* * * * *